US007257433B2

(12) United States Patent
Takamura et al.

(10) Patent No.: US 7,257,433 B2
(45) Date of Patent: Aug. 14, 2007

(54) APPARATUS FOR MEASURING CONCENTRATION OF LIGHT-ABSORBING SUBSTANCE IN BLOOD

(75) Inventors: Yoshiaki Takamura, Tokyo (JP); Naoki Kobayashi, Tokyo (JP); Sunao Takeda, Tokyo (JP); Takashi Usuda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 181 days.

(21) Appl. No.: 10/768,680

(22) Filed: Feb. 2, 2004

(65) Prior Publication Data

US 2004/0176670 A1    Sep. 9, 2004

(30) Foreign Application Priority Data

Jan. 31, 2003    (JP) ............................ P2003-023990

(51) Int. Cl.
*A61B 5/00*    (2006.01)
(52) U.S. Cl. ..................... 600/322; 600/323; 600/330
(58) Field of Classification Search ........ 600/309–310, 600/316, 322–323
See application file for complete search history.

(56) References Cited

U.S. PATENT DOCUMENTS

| | | | |
|---|---|---|---|
| 5,127,406 A | | 7/1992 | Yamaguchi |
| 5,355,882 A | * | 10/1994 | Ukawa et al. ............... 600/323 |
| 5,385,143 A | | 1/1995 | Aoyagi |
| 5,490,523 A | * | 2/1996 | Isaacson et al. ............ 600/323 |
| 6,070,093 A | * | 5/2000 | Oosta et al. ................. 600/310 |
| 6,415,236 B2 | | 7/2002 | Kobayashi et al. |
| 6,714,805 B2 | * | 3/2004 | Jeon et al. ................... 600/323 |

FOREIGN PATENT DOCUMENTS

| | | |
|---|---|---|
| JP | 53-26437 B | 8/1978 |
| JP | 3-71135 B | 11/1991 |
| JP | 5-212016 A | 8/1993 |
| JP | 2002-228579 A | 8/2002 |
| JP | 2002-323444 A | 11/2002 |

OTHER PUBLICATIONS

Takehiko Iijima, et al., "Cardiac output and circulating blood volume analysis by pulse dye-densitometry", Journal of Clinical Monitoring 1997 13: 81-89 (discussed in the specification on p. 1).

(Continued)

*Primary Examiner*—Eric F. Winakur
(74) *Attorney, Agent, or Firm*—Sughrue Mion, PLLC

(57) ABSTRACT

An apparatus for measuring a concentration of a light-absorbing substance in blood is disclosed. A light emitter emits light beams to irradiate a living tissue, each of the light beams being associated with one wavelength which is absorbed by the blood. A first instrument measures first intensities of the light beams, which are to be incident on the living tissue. A second instrument measures second intensities of the light beams, which are transmitted through the living tissue. A first calculator calculates an attenuation variation ratio, which is a ratio of attenuation variations of the respective light beams due to variation of a volume of the blood caused by pulsation, based on the second intensities of the light beams. A second calculator calculates the concentration based on the first intensities, the second intensities, and the attenuation variation ratio.

7 Claims, 11 Drawing Sheets

OTHER PUBLICATIONS

Takasuke Imai, et al., "Measurement of cardiac output by pulse dye-densitometry using indocyanine green", Anesthesiology 1997, 87: 816-822 (discussed in the specification on p. 1).

Takasuke Imai, et al., "Measurement of blood concentration of indocyanine green by pulse dye-densitometry-Comparison with the conventional spectrophotometric method", Journal of Clinical Monitoring 1998, 14: 477-484 (discussed in the specification on p. 1).

* cited by examiner

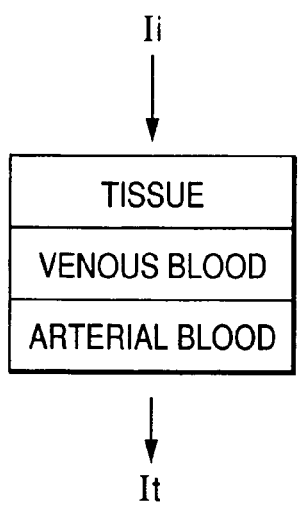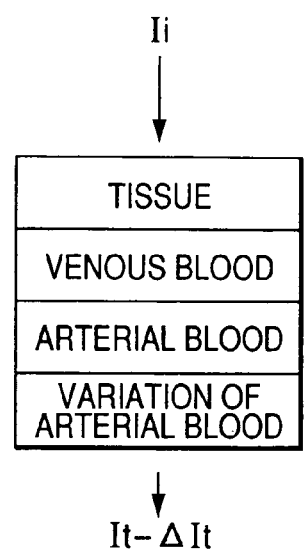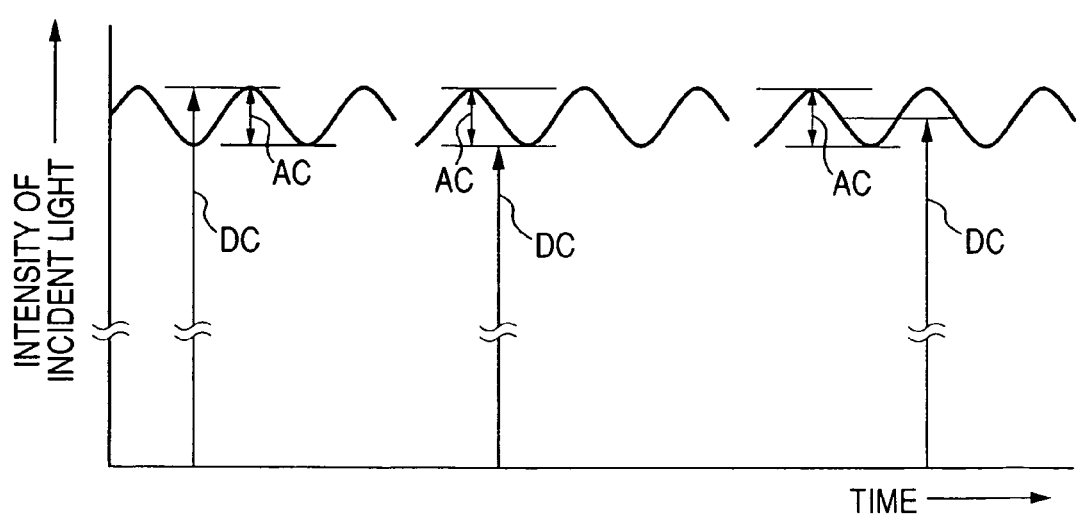

APPARATUS FOR MEASURING CONCENTRATION OF LIGHT-ABSORBING SUBSTANCE IN BLOOD

BACKGROUND OF THE INVENTION

The present invention relates to an improvement in an apparatus for measuring a concentration of a light-absorbing substance in blood which employs pulse photometry as its operating principle: such as a pulse oximeter or an apparatus for measuring a pulse dye-dilution curve.

Pulse photometry goes beyond a pulse oximeter and is currently employed as a pulse dye dilution method. This method is made commercially practical as an apparatus for measuring a cardiac output, a circulating blood volume, a blood plasma disappearance rate of indocyanine green (ICG), and ICG clearance by administering a dye called ICG into blood and determining the concentration of the ICG in blood. This method is described in detail in the following references: Takehiko Iijima, et al. Cardiac output and circulating blood volume analysis by pulse dye-densitometry. J Clin Monit 1997; 13: 81-89; Takasuke Imai, et al. Measurement of cardiac output by pulse dye-densitometry using indocyanine green. Anesthesiology 1997; 87: 816-822; and Takasuke Imai, et al. Measurement of blood concentration of indocyanine green by pulse dye-densitometry-Comparison with the conventional spectrophotometric method. J Clin Monit 1998; 14: 477-484.

Further, the pulse dye dilution method is also applied to measurement of the concentration of abnormal hemoglobin, such as carboxyhemoglobin or methemoglobin, the concentration of hemoglobin, or the glucose level (see e.g., Japanese Patent Publication No. 3-71135B corresponding to U.S. Pat. No. 5,127,406 and Japanese Patent Publication No. 2002-228579A corresponding to U.S. Pat. No. 6,415,236).

Conventionally, for instance, when the concentration of a certain substance in blood is measured through use of two light beams having different wavelengths, the ratio $\Phi 12$ between variation in the attenuation of one wavelength and that in the attenuation of the other wavelength, the variation stemming from pulsation of blood, is determined. The concentration of the substance is calculated on the basis of the phenomenon that a certain constant relationship exists between $\Phi 12$ and the concentration of the substance (see e.g., Japanese Patent Publication No. 53-26437B). Specifically, the concentration of the substance is expressed as:

$$C=F(\Phi 12),$$

where C denotes the concentration of a substance in blood and F denotes a function representing a constant relationship.

In general, when "n" light beams having "n" different wavelengths are used, there are used, at most, "n–1" of attenuation variation ratios $\Phi$ of the respective wavelengths. For instance, if the light beams have three wavelengths, the concentration of a substance is expressed as:

$$C=F(\Phi 12, \Phi 13)$$

through use of a ratio $\Phi 12$ between variation in attenuation of a first wavelength and that in the attenuation of a second wavelength and a ratio $\Phi 13$ between variation in attenuation of the first wavelength and variation in attenuation of a third wavelength.

In the case of a pulse oximeter, the concentration C of a substance in blood is expressed as oxygen saturation in arterial blood $SpO_2$ (a ratio of oxyhemoglobin concentrations to hemoglobin concentrations; that is, $O_2Hb/Hb$). In the case of pulse dye-dilution curve measurement instrument, the concentration C of a substance in blood is expressed as a ratio of dye concentrations Cd to hemoglobin concentrations Hb; that is, a ratio of Cd/Hb.

However, according to such a measurement method, an approximately constant relationship exists between the concentration of a substance and the attenuation variation ratio. However, the relationship involves an individual difference. Even in the case of a single individual, the relationship varies according to a time point when measurement is performed or a measurement location, and variations are responsible for an error in measurement. For instance, in the case of a pulse oximeter, a calculated value varies by about 1% as a result of changing an attached probe from one finger to another finger or raising/lowering a hand, provided that an actual oxygen saturation in arterial blood $SpO_2$ is constant. The following are conceivable as leading causes of the measurement error.

(1) Since blood has a light scattering nature, an attenuation derived from scattering varies depending on the thickness of blood.

(2) Two light beams are present; that is, a light beam passing through blood and another light beam not passing through blood.

When the concentration C of a light-absorbing substance in blood is determined through use of pulse photometry in the previously-described manner, a function taking, as a variable, only the attenuation variation ratio $\Phi$ has hitherto been used. Therefore, no consideration has been given to the dependence of an attenuation derived from scattering on the thickness of blood (not a thickness corresponding to a change but the overall thickness of blood). Further, there exist a light beam passing through blood and another light beam not passing through blood (i.e., a light beam passing through only a living tissue other than blood). Hence, no consideration has been given to the light beam not passing through blood, which in turn causes an error.

SUMMARY OF THE INVENTION

It is therefore an object of the invention to provide an apparatus capable of accurately measuring a concentration of a light-absorbing substance in blood through measurement based on pulse photometry.

According to the present invention, when the concentration of a light-absorbing substance in blood C is calculated through use of a function F, variables of the function F are taken as the attenuation variation ratio $\Phi$ and DC components of attenuations Adc (hereinafter, referred as DC attenuations Adc), with regard to the entire thickness of blood and the thickness of a living tissue other than blood. Therefore, the concentration C is expressed by the following function F.

$$C=F(\Phi, Adc)$$

Here, when measurement is performed by light beams of "n" wavelengths, "n–1" for $\Phi$ and "n" for Adc are used at most. For instance, when measurement is performed through use of three wavelengths, the function F is expressed as follows through use of DC attenuations Adc1, Adc2, Adc3 for respective wavelengths.

$$C=F(\Phi 12, \Phi 13, Adc1, Adc2, Adc3)$$

The DC attenuation Adc is expressed as follows through use of an incident light intensity li and a transmitted light intensity lt.

$$Adc = \log(li/lt) = \log li - \log lt$$

Here, lt denotes the intensity of the light having passed through a living body, which can be measured consecutively. In contrast, the intensity of incident light li must be ascertained in advance through measurement. A method for ascertaining li is described in Japanese Patent Publication No. 5-212016A corresponding to U.S. Pat. No. 5,385,143. According to this method, a phantom (i.e., a sample member simulating a living body) having a known light-absorbing characteristic is sandwiched by a probe, and the intensity of light having passed through the phantom is measured, thereby determining the intensity of incident light.

At wavelengths of 660 nm, 805 nm, and 940 nm, hemoglobin absorbs light but water essentially does not absorb light. Therefore, when a living tissue is exposed to light beams having these wavelengths, DC attenuations are primarily relevant to the quantity of blood flowing through a location to be measured. At a wavelength 1300 nm, a small quantity of light is absorbed by hemoglobin and a large quantity of light is absorbed by water. The DC attenuations are primarily relevant to the thickness of a living tissue (i.e., the quantity of water content). Therefore, the accuracy of measurement of concentration of a light-absorbing substance in blood can be enhanced, by measuring the DC attenuations at these wavelengths, substituting results of measurement as variations into formulae, and correcting errors attributable to error factors (1) and (2).

Further, according to the invention, in view of the fact that a constant relationship exists between the DC attenuations and the DC transmitted light intensities (DC components of the transmitted light intensities), the concentration of a light-absorbing substance in blood C is expressed by the following equation through use of the function F1 using variables as Φ and DC, in consideration of the DC transmitted light intensities.

$$C = F1(\Phi, DC)$$

Here, when measurement is performed through use of "n" kinds of light beams having "n" kinds of wavelengths, "n−1" for Φ and "n" for DC are used at most. For instance, when measurement is performed through use of three wavelengths, the function F1 is expressed as follows through use of DC transmitted light intensities DC1, DC2, DC3 for respective wavelengths.

$$C = F1(\Phi 12, \Phi 13, DC1, DC2, DC3)$$

As mentioned above, even when there is used the function using, as variables, the attenuation variation ratio Φ and the DC transmitted light intensities DC, the accuracy of measurement of concentration of a light-absorbing substance in blood can be enhanced similarly.

Specifically, in order to achieve the above object, according to the invention, there is provided an apparatus for measuring a concentration of a light-absorbing substance in blood, comprising:

a light emitter, which emits light beams to irradiate a living tissue, each of the light beams being associated with one wavelength which is absorbed by the blood;

a first instrument, which measures first intensities of the light beams, which are to be incident on the living tissue;

a second instrument, which measures second intensities of the light beams, which are transmitted through the living tissue;

a first calculator, which calculates an attenuation variation ratio, which is a ratio of attenuation variations of the respective light beams due to variation of a volume of the blood caused by pulsation, based on the second intensities of the light beams; and a second calculator, which calculates the concentration based on the first intensities, the second intensities, and the attenuation variation ratio.

Preferably, the second calculator calculates DC components of attenuations of the light beams, based on the first intensities and the second intensities. The second calculator obtains the concentration, based on the DC components and the attenuation variation ratio.

Here, it is further preferable that the second calculator calculates a DC attenuation ratio which is a ratio of the DC components. The second calculator obtains the concentration, based on the DC attenuation ratio and the attenuation variation ratio.

Alternatively, it is preferable that the second calculator calculates DC components of intensities of the light beams transmitted through the living tissue, based on the first intensities and the second intensities. The second calculator obtains the concentration, based on the DC components and the attenuation variation ratio.

Here, it is further preferable that the second calculator calculates a DC transmission ratio which is a ratio of the DC components. The second calculator obtains the concentration, based on the DC transmission ratio and the attenuation variation ratio.

Preferably, the light emitter comprises light emitting elements, and a controller which controls a current value or a voltage value supplied to the light emitting elements. The second calculator corrects the first intensities in accordance with the current value or the voltage value.

Preferably, the second instrument measures third intensities of the light beams which are transmitted through a phantom placed between the light emitter and the second instrument. The first instrument obtains the first intensities based on the third intensities.

Here, it is further preferable that the first instrument comprises a sensor which senses whether the phantom is placed between the light emitter and the second instrument. The first instrument begins calculation to obtain the first intensities when the sensor senses that the phantom is placed between the light emitter and the second instrument.

According to the invention, there is also provided an apparatus for measuring a concentration of a light-absorbing substance in blood, comprising:

a light emitter, which emits (n) kinds of light beams to irradiate a living tissue, each of the light beams being associated with one wavelength which is absorbed by the blood;

a first instrument, which measures (n) kinds of first intensities of the light beams, which are to be incident on the living tissue;

a second instrument, which measures (n) kinds of second intensities of the light beams, which are transmitted through the living tissue;

a first calculator, which calculates, at most, (n−1) kinds of attenuation variation ratios, which is a ratio of attenuation variations of the respective light beams due to variation of a volume of the blood caused by pulsation, based on the second intensities of the light beams; and a second calculator, which calculates, at most, (n) kinds of DC components of attenuations of the light beams, based on the first intensities and the second intensities, and obtains the concentration based on the DC components and the attenuation variation ratio, wherein (n) is an integer which is three or more.

According to the invention, there is also provided an apparatus for measuring a concentration of a light-absorbing substance in blood, comprising:

a light emitter, which emits (n) kinds of light beams to irradiate a living tissue, each of the light beams being associated with one wavelength which is absorbed by the blood;

a first instrument, which measures (n) kinds of first intensities of the light beams, which are to be incident on the living tissue;

a second instrument, which measures (n) kinds of second intensities of the light beams, which are transmitted through the living tissue;

a first calculator, which calculates, at most, (n−1) kinds of attenuation variation ratios, which is a ratio of attenuation variations of the respective light beams due to variation of a volume of the blood caused by pulsation, based on the second intensities of the light beams; and a second calculator, which calculates, at most, (n) kinds of DC components of intensities of the light beams transmitted through the living tissue, based on the first intensities and the second intensities, and obtains the concentration based on the DC components and the attenuation variation ratio, wherein (n) is an integer which is three or more.

In the above apparatuses, it is preferable that the light emitter emits a light beam having a wavelength which is absorbed by a living tissue other than the blood.

According to the above configurations, the concentration of a light-absorbing substance in blood can be measured accurately on the basis of the principle of pulse photometry.

BRIEF DESCRIPTION OF THE DRAWINGS

The above object and advantages of the present invention will become more apparent by describing in detail preferred exemplary embodiments thereof with reference to the accompanying drawings, wherein:

FIGS. 3A and 3B are schematic views for explaining a relationship between the intensity of incident light and the intensity of transmitted light obtained when a living body is exposed to light;

FIGS. 4A to 4C are views for explaining how to obtain DC components of transmitted light intensities;

DETAILED DESCRIPTION OF THE INVENTION

A first embodiment of the invention will now be described. A first embodiment is directed to an apparatus for measuring a hemoglobin concentration.

Figure 2:
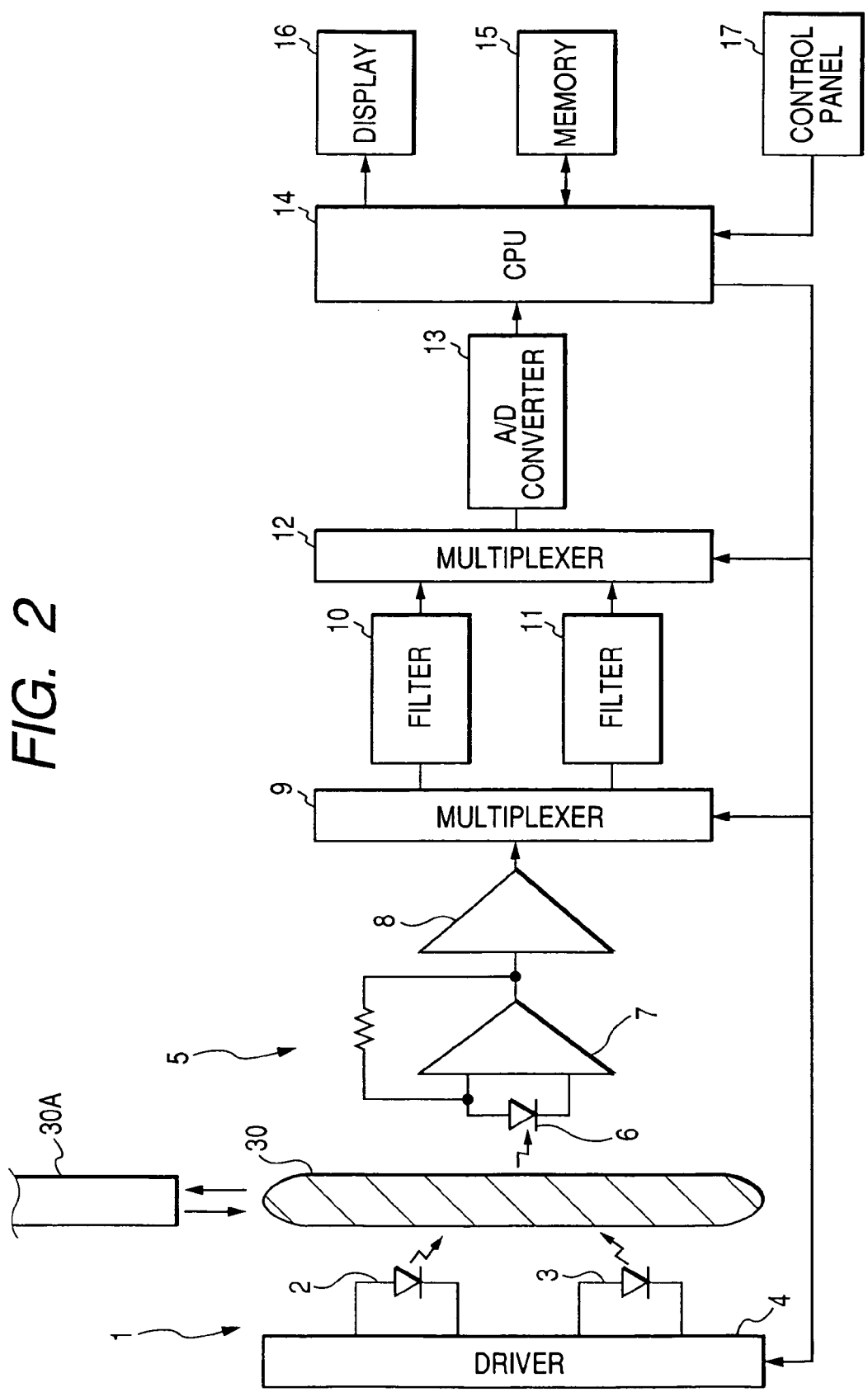
FIG. 2 is a block diagram of the apparatus of the first embodiment.

FIG. 2 is a block diagram showing the overall configuration of the apparatus of the embodiment. A light emitter 1 comprises: LEDs 2, 3 for generating light beams having two different wavelengths; and a driver 4 for driving the LEDs 2, 3. The wavelength of a light beam originating from the LED 2 is taken as a first wavelength, and the wavelength of a light beam originating from the LED 3 is taken as a second wavelength. In this apparatus, the first wavelength is 1300 nm, and the second wavelength is 805 nm.

A light receiver 5 comprises: a photodiode 6 disposed opposite the LEDs 2, 3; a current/voltage converter 7 for converting an output electric current from the photodiode 6 into a voltage signal; and an amplifier 8.

A multiplexer 9 is a circuit for distributing a signal sent from the amplifier 8 to a filter 10 or a filter 11. The filters 10, 11 are circuits for eliminating noise from signals corresponding to intensities of transmitted light beams having respective wavelengths. Output timings of the output signals are controlled by a multiplexer 12, and the signals are then delivered to an A/D converter 13. The A/D converter 13 is a circuit for converting the signal output from the multiplexer 12 into a digital signal.

A CPU 14 is a circuit for controlling the driver 4, the multiplexer 9, and the multiplexer 12 and performing operation on the basis of a signal output from the A/D converter 13.

Memory 15 stores a program for use with processing to be performed by the CPU 14 and data output from the CPU 14.

A display 16 displays the data output from the CPU 14, and a control panel 17 is equipped with a plurality of switches (including a calibration switch and a measurement switch, which will be described later) and a plurality of keys, and outputs to the CPU 14 a signal corresponding to an operator's operation.

Figure 1:
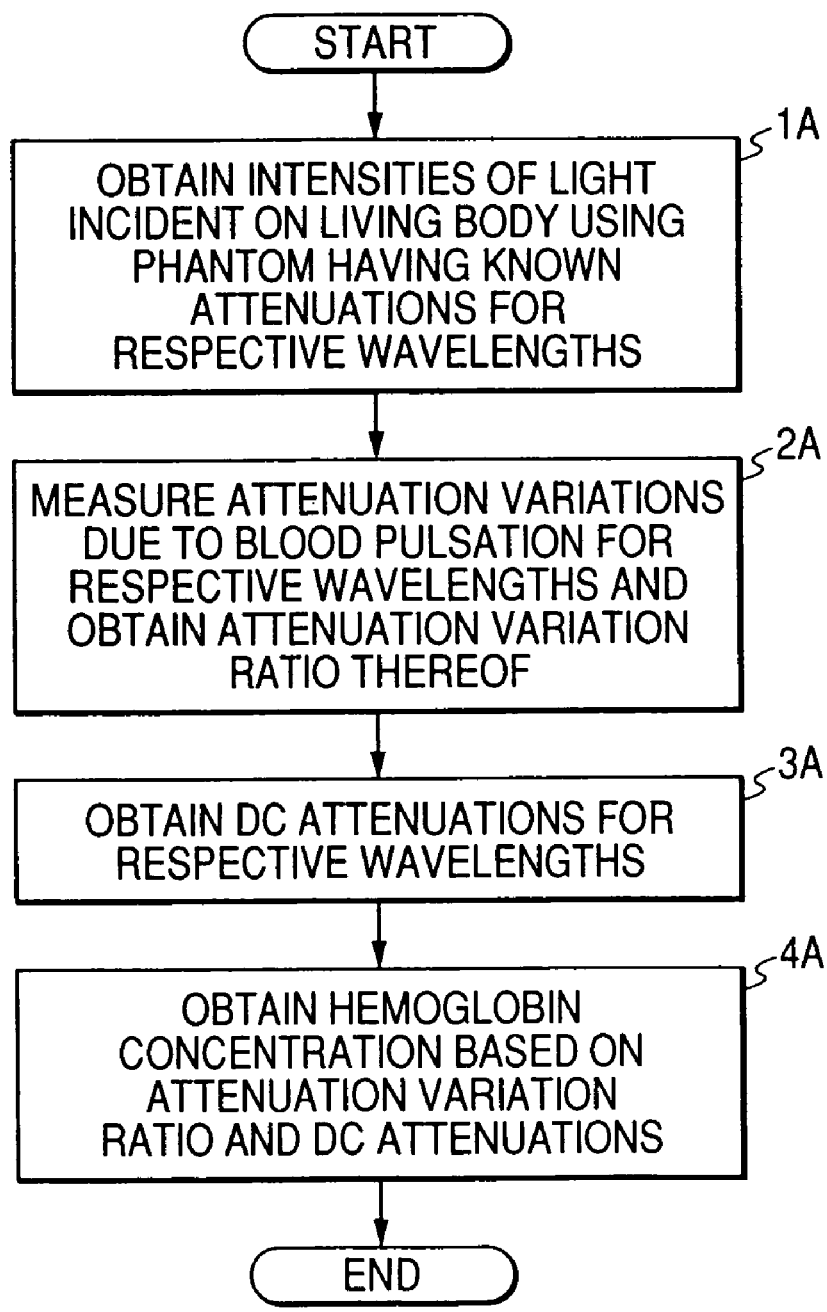
FIG. 1 is a flow chart for explaining a processing flow of an apparatus according to a first embodiment of the invention.

A probe of this apparatus to be attached to a living body is equipped with the LEDs 2, 3 and the photodiode 6. A living body (e.g., a finger tip or an ear flap) 30 is nipped between the LEDs 2, 3 and the photodiode 6. Next, operation of the apparatus will be described by reference to FIG. 1.

In step 1A, the intensity of the light incident on a living body is measured. Specifically, the intensity of light radiated from the LEDs 2, 3 of the probe onto the living body is determined. In the embodiment, the intensity of incident light is determined through use of a phantom 30A having a known light-absorbing characteristic. For instance, a milky white acrylic plate is suitable as the phantom 30A.

First, the operator places the phantom 30A at a predetermined position between the LEDs 2, 3 of the probe and the photodiode 6 and instructs the CPU 14 to start measuring the intensity of the incident light by operating the calibration switch of the control panel 17. As a result, the LEDs 2, 3 generate light beams having respective wavelengths, and the light beams reach the photodiode 6 after having passed through the phantom 30A and are converted into electric signals. The signals are processed in subsequent stages by the current/voltage converter 7, the amplifier 8, the multiplexer 9, the filters 10, 11, the multiplexer 12, and the A/D converter 13. The signals then reach the CPU 14, and the signals are stored in the memory 15 as transmitted light intensities ltcal1, ltcal2 of respective wavelengths. The CPU 14 performs calculating operation by substituting the thus-measured ltcal1, ltcal2 into following Equations (1) and (2), thereby determining the incident light intensities lical1, lical2 with respect to the phantom 30A.

$$lical1 = ltcal1 \cdot \exp(Af1) \quad (1)$$

$$lical2 = ltcal2 \cdot \exp(Af2) \quad (2)$$

Figure 11:
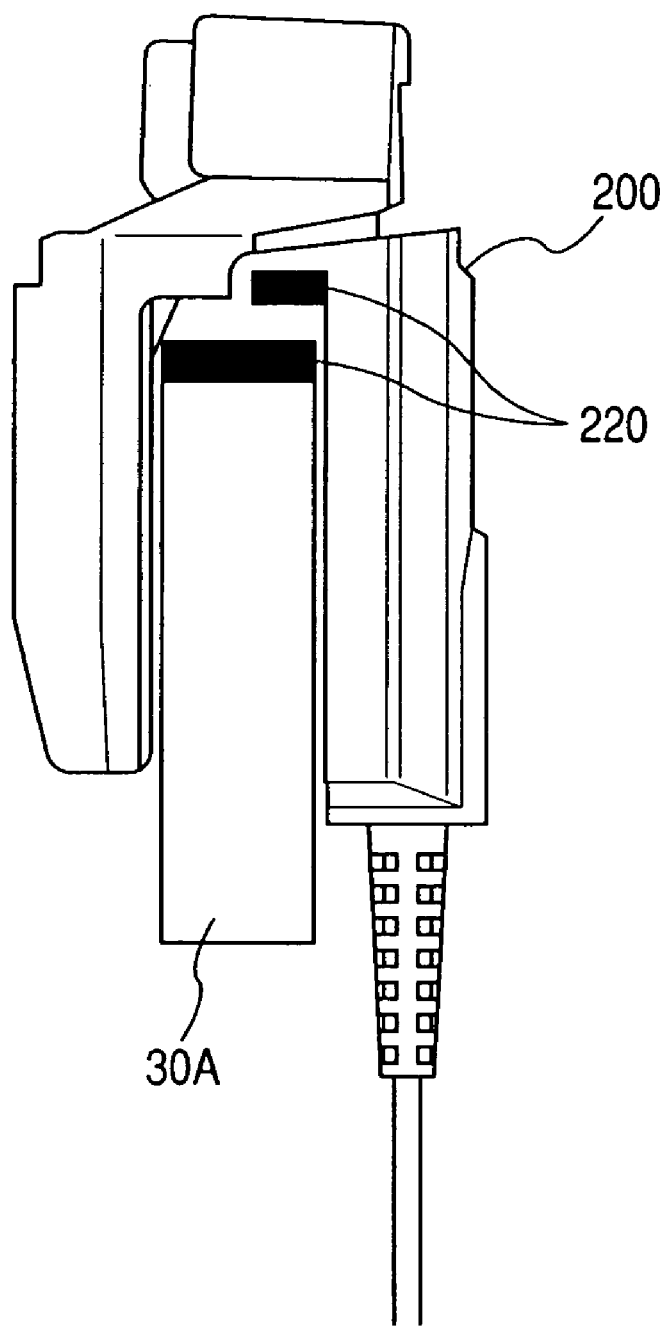
FIG. 11 is a schematic view showing a first modified example of the apparatus of the first embodiment.

In the equations, Af1, Af2 denote known attenuations of the phantom 30A which are achieved at the respective wavelengths and stored in the memory 15 in advance. Computation results are also stored in the memory 15. The computation results lical1, lical2 are written into a predetermined area in the memory 15. If the values lical1, lical2 that have been measured last time are available, the values are rewritten. The most current values lical1, lical2 are used for calculating operation to be performed in step 3A, which will be described later. Therefore, step 1A is for calibrating the intensity of incident light lical Computation of the intensity of incident light lical is performed when the operator attaches the probe to the phantom 30A and presses the calibration switch. However, as shown in FIG. 11, any kind of a sensor (optical, mechanical or magnetic) 220 may be provided in a probe 200 and a phantom 30A and arranged such that, when the probe 200 is attached to the phantom 30A, the sensor 220 detects the attaching action and the CPU 14 starts processing such as that mentioned previously, to thereby calculate the intensity of incident light lical.

Figure 12:
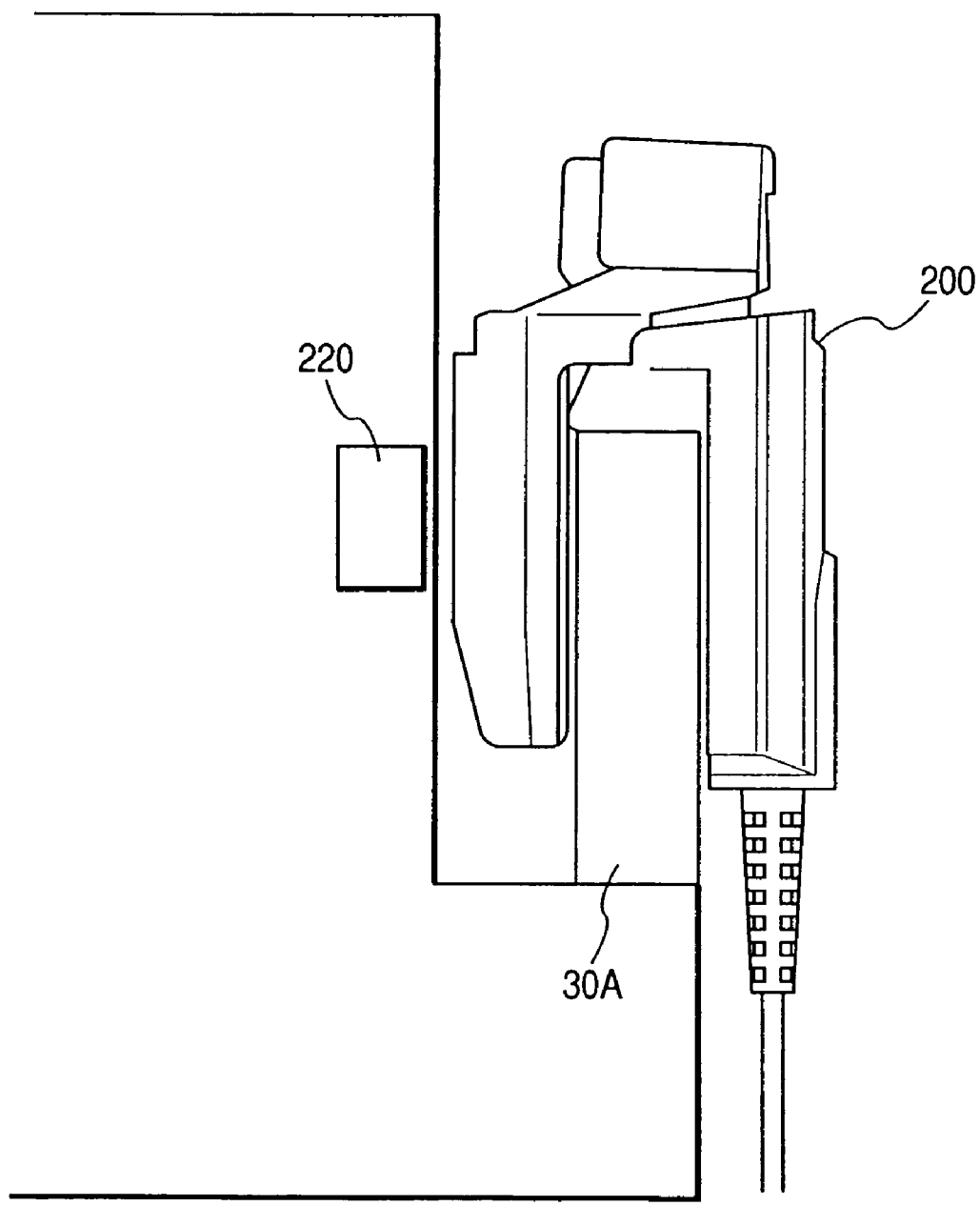
FIG. 12 is a schematic view showing a second modified example of the apparatus of the first embodiment.

Alternatively, as shown in FIG. 12, the phantom 30A per se may be formed into a holder which holds a probe 200. The foregoing sensor 220 may be provided on such a holder. When the probe 200 has been housed in the holder (as a matter of course, a portion of the phantom 30A is nipped between the LEDs 2, 3 and the photodiode 6), the sensor 220 may detect the holding action, whereupon the CPU 14 may calculate the intensity of incident light lical.

When having been used over a long period of time, the light-emitting element, such as an LED, undergoes a drop in emission intensity. Emission intensity is also changed by stains on the surface of the probe. Hence, difficulty is encountered in continuous use of the emission intensity of the probe that has been set at the time of shipment. A better arrangement is to calibrate the intensity of incident light lical immediately before measurement.

In step 2A, the probe is attached to the living body 30, and variations in the attenuations at the respective wavelengths caused by pulsation of blood are measured, and the ratio $\Phi$ between the variations in the attenuations is determined.

Processing pertaining to this step is started by the operator operating the measurement switch of the control panel 17. At this time, the CPU 14 determines the ratio $\Phi 12$ between variation $\Delta A1$ in an attenuation A1 of the first wavelength and variation $\Delta A2$ in an attenuation A2 of the second wavelength on the basis of the signal indicating the transmitted light intensities lt1, lt2 output from the A/D converter 13. Specifically, following Equation (3) is calculated, and a result of computation is stored in the memory 15.

$$\Phi 12 = \Delta A1/\Delta A2 = (AC1/DC1)/(AC2/DC2) \quad (3)$$

Here, DC1 denotes a DC component of the pulsating transmitted light intensity lt1, and DC2 denotes a DC component of the pulsating transmitted light intensity lt2. Both DC1 and DC2 are called DC transmitted light intensities. Moreover, AC1 denotes an AC component of the pulsating transmitted light intensity lt1, and AC2 denotes an AC component of the pulsating transmitted light intensity lt2. Both lt1 and lt2 are called AC transmitted light intensities.

Equation (3) is obtained in the following manner. As shown in FIG. 3A, a living body can be considered to be constituted of arterial blood, venous blood, and tissues other than blood. When the living body is exposed to light having the incident light intensity li, light having the transmitted light intensity lt is measured. At this time, an attenuation A caused by the living body is expressed by following Equation (4) on the basis of the Lambert-Beer law.

$$A = \log(li/lt) = \log li - \log lt \quad (4)$$

Next, as shown in FIG. 3B, given that a variation, which would be caused by a change in the thickness of a layer of arterial blood, is taken as $\Delta lt$, a corresponding variation in the intensity of transmitted light is expressed as $lt - \Delta lt$. At this time, a variation $\Delta A$ is added to the attenuation caused by the living body and expressed by following Equation (5).

$$A + \Delta A = \log[li/(lt - \Delta lt)] = \log li - \log(lt - \Delta lt) \quad (5)$$

A is deleted from Equations (4) and (5), thereby determining $\Delta A$. At this time, $\Delta A$ is expressed as follows by an equation which does not use the incident light intensity li.

$$\Delta A = \log lt - \log(lt - \Delta lt) = \log[lt/(lt - \Delta lt)] \quad (6)$$

Equation (6) is transformed as follows:

$$\Delta A = \log\{1/[1 - (\Delta lt/lt)]\} \quad (7)$$

Here, ($\Delta lt/lt$) assumes a value which is considerably smaller than 1 (because the variation $\Delta lt$ of the transmitted light intensity lt derived from pulsation of an arterial blood layer of a living body is considerably smaller than the transmitted light intensity lt). Equation (7) can be made approximate by following Equation (8).

$$\Delta A = \Delta lt/lt \quad (8)$$

Therefore, following Equation (9) can be obtained from a definition equation of $\Phi 12$ and Equation (8).

$$\Phi 12 = \Delta A1/\Delta A2 = (\Delta lt1/lt1)/(\Delta lt2/lt2) \quad (9)$$

As a result, logarithmic operation becomes obviated. Equation (9) is considered to be obtained when the transmitted light intensities are changed by $\Delta lt1$, $\Delta lt2$ with reference to lt1, lt2.

As shown in FIG. 4A, under the assumptions that a peak value of the pulsating transmitted light intensity lt is taken as a DC transmitted light intensity DC and that a difference between the peak value and a bottom value (i.e., a maximum variation) is taken as an AC transmitted light intensity AC, the transmitted light intensity is considered to have changed by AC with reference to DC. Therefore, there is attained $\Delta lt/lt = AC/DC$, and Equation (9) is transformed as follows.

$$\Phi 12 = \Delta A1/\Delta A2 = (AC1/DC1)/(AC2/DC2)$$

In short, Equation (3) is obtained.

Here, the peak value of the transmitted light intensity is taken as the DC transmitted light intensity DC. However, AC is considerably smaller than DC. As shown in FIG. 4B, even when the DC transmitted light intensity DC is taken as the bottom value of the pulsating transmitted light intensity It, Equation (3) stands. As shown in FIG. 4C, even when the DC transmitted light intensity DC is taken as a mean value between the peak value and the bottom value (i.e., an intermediate value between the peak value and the bottom value), Equation (3) stands.

As mentioned above, the DC transmitted light intensity DC may be any value located between the peak value and the bottom value. Accordingly, the transmitted light intensity It achieved at a time point where AC transmitted light intensity is achieved or at immediate before or after that time point may be used as it is.

In this step, computation of $\Phi 12$ is performed per each wave of the pulsating transmitted light intensities It1, It2; that is, per each heartbeat.

In subsequent step 3A, the DC attenuations Adc1, Adc2 of the respective wavelengths are determined. Here, the CPU 14 calculates the DC attenuations Adc1, Adc2 of the respective wavelengths by substituting, into following Equations (10) and (11), the incident light intensities lical1, lical2 determined in step 1A and the DC transmitted light intensities DC1, DC2 determined in step 2A.

$$Adc1 = \log(lical1/DC1) = \log lical1 - \log DC1 \quad (10)$$

$$Adc2 = \log(lical2/DC2) = \log lical2 - \log DC2 \quad (11)$$

When the apparatus has a circuit configuration which does not cause any change in the current flowing through the light-emitting elements (LEDs 2, 3), the incident light intensities lical1, lical2 determined in step 1A are used in their unmodified forms.

However, in view of the fact that the living tissue involves an individual difference, a difference may arise between the electric currents Ccal1, Ccal2 flowing to the light-emitting elements when the incident light intensity measurement (i.e., at the time of calibration) is performed through use of the phantom 30A, and electric currents Cmeas1, Cmeas2 flowing to the light-emitting elements when an attenuation of the living body is measured (i.e., at the time of measurement). In a case where the apparatus is provided with a circuit configuration for performing adjustment so as to achieve an optimum transmitted light intensity by changing the electric current of the light-emitting element, the CPU 14 employs, as the intensity of incident light, the values liA1, liA2 corrected according to the electric current flowing through the light-emitting elements. liA1 and liA2 are expressed as follows.

$$liA1 = lcal1 \cdot Cmeas1/Ccal1 \quad (12)$$

$$liA2 = lcal2 \cdot Cmeas2/Ccal2 \quad (13)$$

In this step, computation of the DC attenuations Adc1, Adc2 is performed per each wave of the pulsating transmitted light intensities It1, It2; that is, per each heartbeat.

In step 4A, the CPU 14 calculates the concentration of hemoglobin Hbdc through use of following Equation (14), which employs, as variables, the $\Phi 12$ determined in step 2A and the DC attenuations Adc1, Adc2 determined in step 3A.

$$Hbdc = a1 \cdot \Phi 12 + b1 + c1 \cdot Adc2/Adc1 \quad (14)$$

Coefficients a1, b1, c1 of Equation (14) are values which have been determined beforehand by the method of least squares so as to minimize a difference between the hemoglobin concentration Hbdc determined by calculating a certain population (e.g., data pertaining to ten selected persons) through use of Equation (14) and the accurate concentration of hemoglobin Hbs measured through blood sampling and the cyanmethemoglobin method.

Here, in order to exhibit the advantageous effect of the apparatus, the concentration of hemoglobin calculated through use of only the attenuation variation ratio $\Phi 12$ of the pulse wave is compared with the concentration of hemoglobin determined by blood sampling. Further, the concentration of hemoglobin calculated by the apparatus through use of $\Phi 12$ and the DC attenuations Adc1, Adc2 is compared with the concentration of hemoglobin determined by blood sampling.

When only the attenuation variation ratio $\Phi 12$ is used, the concentration of hemoglobin is calculated by Equation (15).

$$Hbp = a2 \cdot \Phi 12 + b2 \quad (15)$$

Figure 5A:
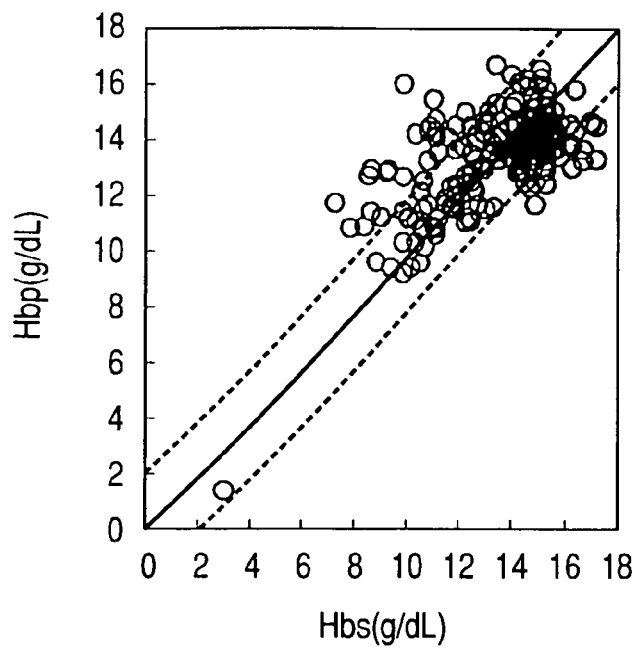
FIGS. 5A and 5B are views for explaining the advantageous effect obtained by the apparatus of the first embodiment.

Coefficients a2, b2 employed in this case are also determined in advance on the basis of the data pertaining to the population by the method of least squares. FIG. 5A shows a correlation between the hemoglobin concentration Hbp calculated through use of Equation (15) and the hemoglobin concentration Hbs measured by blood sampling.

Figure 5B:
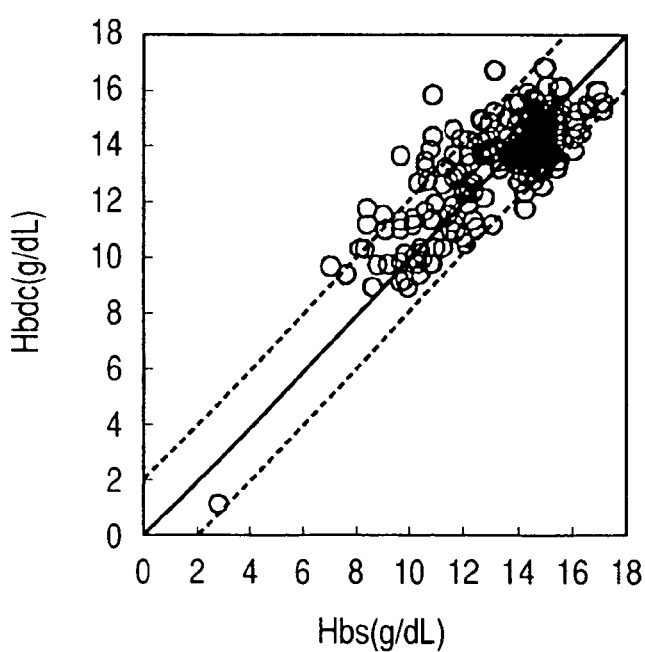

FIG. 5B shows a correlation between the hemoglobin concentration Hbdc determined by the apparatus of the embodiment based on Equation (14) through use of the DC attenuations and the hemoglobin concentration Hbs measured by blood sampling. As is evident from a comparison between the drawings, an improvement is achieved in a match between the hemoglobin concentration determined by the apparatus and that determined by blood sampling, by substituting the DC attenuations into the formula.

The following equation may be employed in lieu of Equation (14).

$$Hbdc = a3 \cdot \Phi 12 + b3 + c3 \cdot Adc2 + d3 \cdot Adc1 \quad (16)$$

Coefficients a3 to d3 of this equation have been determined beforehand in the same manner as mentioned previously.

A constant reverse correlation exists between the DC attenuations Adc1, Adc2 and the DC transmitted light intensities DC1, DC2. Hence, there is yielded the same effect as that achieved by performing calculating operation through use of the DC transmitted light intensities in their unmodified forms without use of the DC attenuations. In this case, the DC transmitted light intensity is proportional to the intensity of the light incident on the probe. Therefore, the incident light intensities lical1, lical2 must be corrected, while being normalized, by a specific current value flowing into the light-emitting elements (the LEDs 2, 3). The corrected DC transmitted light intensities ltcomp1, ltcomp2 for the respective wavelengths are calculated by following Equations (17) and (18).

$$ltcomp1 = DC1(lical1/lstd1)(Cmeas1/Ccal1) \quad (17)$$

$$ltcomp2 = DC2(lical2/lstd2)(Cmeas2/Ccal2) \quad (18)$$

where, DC1, DC2 denote measured DC transmitted light intensities; lical1, lical2 denote incident light intensities calculated at the time of calibration; lstd1, lstd2 denote standard incident light intensities; Cmeas1, Cmeas2 denote current values flowing into light-emitting elements obtained when a living body is measured; and Ccal1, Ccal2 denote current values flowing into the light-emitting elements obtained at the time of calibration of the incident light intensities.

Therefore, following Equations (19) and (20) may be employed in place of Equations (14) and (16).

$$Hbdc = a4 \cdot \Phi 12 + b4 + c4 \cdot lt\text{comp1}/lt\text{comp2} \quad (19)$$

$$Hbdc = a5 \cdot \Phi 12 + b5 + c5 \cdot lt\text{comp1} + d5 \cdot lt\text{comp2} \quad (20)$$

Here, coefficients a4 to c4 in Equation (19) and coefficients a5 to d5 in Equation (20) are determined in advance by the same method as that used for determining the coefficients of Equation (14).

Even in this step, computation of Hbdc is performed per each wave of the pulsating transmitted light intensities lt1, lt2; that is, per each heartbeat. The CPU 14 stores the thus-determined Hbdc into the memory 15 and displays the same on the display 16.

According to the apparatus of the embodiment, the concentration of hemoglobin is calculated through use of the DC attenuation or DC transmitted light intensity achieved at the first wavelength 1300 nm at which light is absorbed by a living tissue other than blood, and the DC attenuation or DC transmitted light intensity achieved at the second wavelength 805 nm at which light is absorbed by blood. As a result, consideration has been given to the blood flowing through an area to be measured and the thickness of the entire living tissue formed from a tissue other than blood, whereby the concentration of hemoglobin can be measured accurately.

In the embodiment, the first wavelength can be made to red light (having a wavelength of, e.g., 660 nm), and the second wavelength can be made to infrared light (having a wavelength of, e.g., 940 nm), thereby determining the concentration of oxyhemoglobin. Thus, the apparatus can be applied to measurement of oxygen saturation in arterial blood.

A second embodiment of the invention will now be described. The second embodiment is directed to an apparatus for a carboxyhemoglobin concentration.

Figure 6:
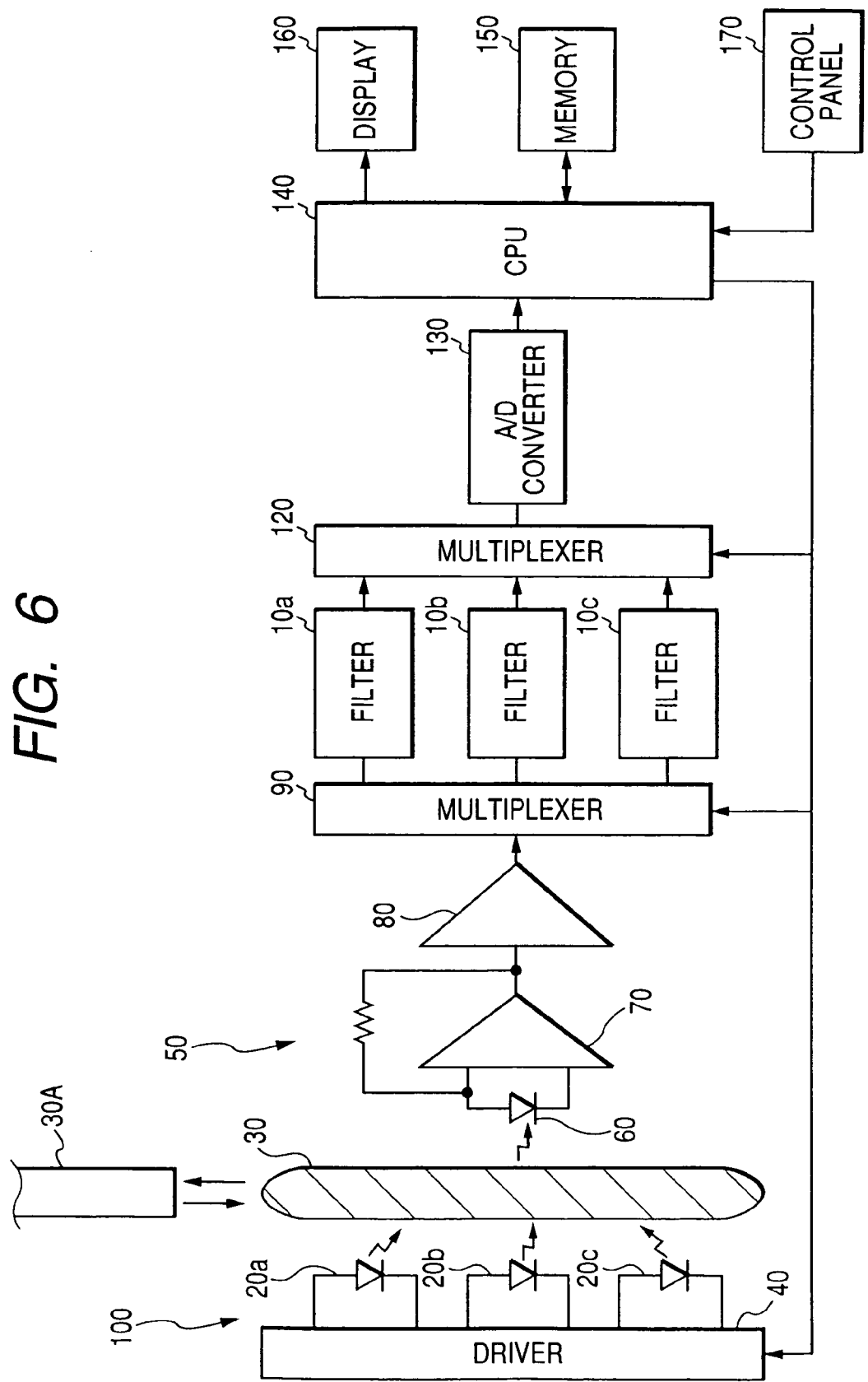
FIG. 6 is a block diagram of an apparatus according to a second embodiment of the invention.

FIG. 6 is a block diagram showing the overall configuration of the apparatus of the embodiment. A light emitter 100 comprises: LEDs 20a, 20b, and 20c for generating light beams of three different wavelengths; and a driver 40 for driving the LEDs 20a, 20b, and 20c.

The wavelength of a light beam originating from the LED 20a is taken as a first wavelength; the wavelength of a light beam originating from the LED 20b is taken as a second wavelength; and the wavelength of a light beam originating from the LED 20c is taken as a third wavelength. In this apparatus, the first wavelength is 940 nm; the second wavelength is 660 nm; and the third wavelength is 620 nm.

A light receiver 50 comprises: a photodiode 60 disposed opposite the LEDs 20a, 20b, and 20c; a current/voltage converter 70 for converting an output electric current from the photodiode 60 into a voltage signal; and an amplifier 80.

A multiplexer 90 is a circuit for distributing a signal sent from the amplifier 80 to one of among three filters; that is, a filter 10a, a filter 10b, and a filter 10c. The filters 10a, 10b, and 10c are circuits for eliminating noise from signals corresponding to intensities of transmitted light beams having respective wavelengths. Output timings of the output signals are controlled by a multiplexer 120, and the signals are then delivered to an A/D converter 130. The A/D converter 130 is a circuit for converting the signal output from the multiplexer 120 into a digital signal.

A CPU 140 is a circuit which outputs control signals to the driver 40, the multiplexer 90, and the multiplexer 120, to thus control the same and which performs operation on the basis of a signal output from the A/D converter 130.

Memory 150 stores a program for use with processing to be performed by the CPU 140 and data output from the CPU 140.

Figure 7:
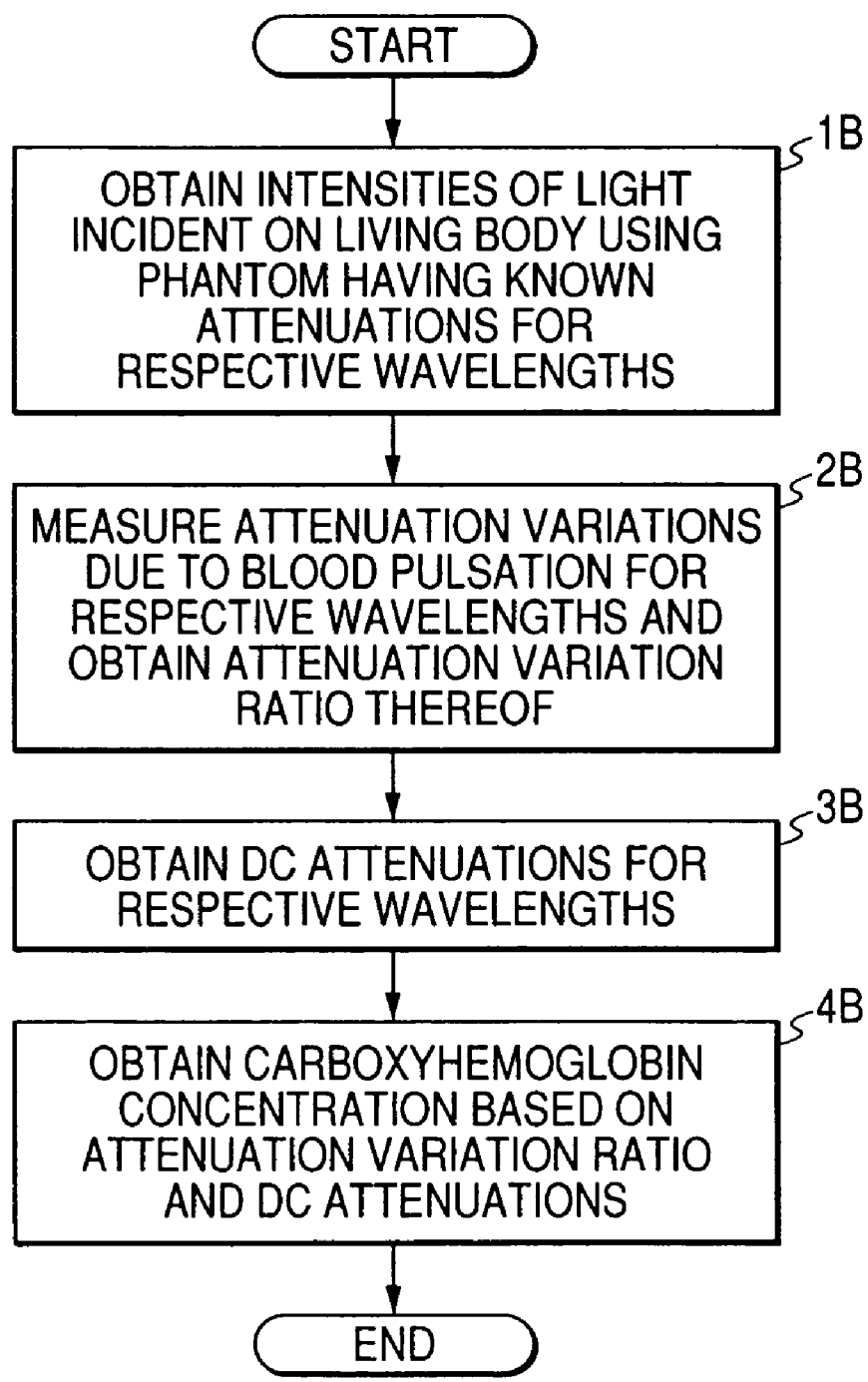
FIG. 7 is a flow chart for explaining a processing flow of the apparatus of the second embodiment.

A display 160 displays the data output from the CPU 140, and a control panel 170 is equipped with a plurality of switches (including a calibration switch and a measurement switch, which will be described later) and a plurality of keys, and outputs a signal corresponding to an operator's operation to the CPU 140. A probe of this apparatus is equipped with the LEDs 20a, 20b, and 20c and the photodiode 60. The living body 30 is nipped between the LEDs 20a, 20b, and 20c and the photodiode 60. Next, operation of the apparatus will be described by reference to FIG. 7.

In step 1B, the intensity of the light incident on the living body 30 is measured. Specifically, the intensity of light radiated from the three LEDs 20a, 20b, and 20c of the probe onto the living body 30 is determined. As in the step 1A to be performed by the apparatus of the first embodiment, the operator places the phantom 30A at a predetermined position between the LEDs 20a, 20b, and 20c of the probe and the photodiode 60 and instructs the CPU 140 to start measuring the intensity of the incident light by operating the calibration switch. The CPU 140 performs calculating operation of the following equations by substituting the light intensities ltcal1, ltcal2, and ltcal3 of the three wavelengths of the light beams having passed through the phantom 30A, thereby determining incident light intensities lical1, lical2, and lical3 of three wavelengths and storing them into the memory 150.

$$lical1 = ltcal1 \cdot \exp(Af1)$$

$$lical2 = ltcal2 \cdot \exp(Af2)$$

$$lical3 = ltcal3 \cdot \exp(Af3)$$

Here, Af1, Af2, and Af3 denote known attenuations of the phantom 30A achieved at the respective wavelengths and are stored in the memory 150 in advance.

In step 2B, the operator attaches the probe to the living body 30, thereby actuating the measurement switch. As a result, the CPU 140 measures variations in the attenuations at the respective wavelengths caused by pulsation of blood of the living body 30 and the ratio $\Phi$ between the variations in the attenuations.

In this step, the CPU 140 determines the DC transmitted light intensities and AC transmitted light intensities of the respective wavelengths in the same manner as in the case of step 2A of the first embodiment and determines attenuation variation ratios of the respective wavelengths through use of the intensities. Here, the light beams of three wavelengths are used, and hence, $\Phi 12$ and $\Phi 13$ are determined by calculating following Equations (21) and (22), and results of the computation are stored in the memory 150.

$$\Phi 12 = \Delta A1/\Delta A2 = (AC1/DC1)/(AC2/DC2) \quad (21)$$

$$\Phi 13 = \Delta A1/\Delta A3 = (AC1/DC1)/(AC3/DC3) \quad (22)$$

Here, $\Phi 12$ denotes a ratio between variation $\Delta A1$ in an attenuation A1 of the first wavelength and variation $\Delta A2$ in an attenuation A2 of the second wavelength; $\Phi 13$ denotes a ratio between variation $\Delta A1$ in the attenuation A1 of the first wavelength and variation $\Delta A3$ in an attenuation A3 of the third wavelength; DC1, DC2, DC3 respectively denote DC transmitted light intensities obtained at transmitted light intensities lt1, lt2, and lt3 of the first through third wavelengths; and AC1, AC2, AC3 respectively denote AC transmitted light intensities obtained at the transmitted light intensities lt1, lt2, and lt3 of the first through third wavelengths.

In this step, computation of Φ12, Φ13 is performed per each wave of the pulsating transmitted light intensities lt1, lt2, lt3; that is, per each heartbeat.

In subsequent step 3B, the DC attenuations Adc1, Adc2, Adc3 of the respective wavelengths are determined. Here, the CPU 140 calculates the DC attenuations Adc1, Adc2 of the respective wavelengths by substituting, into following Equations (23) to (25), the incident light intensities lical1, lical2, and lical3 determined in step 1B and the DC transmitted light intensities DC1, DC2, and DC3 determined in step 2B.

$$Adc1=\log(lical1/DC1)=\log lical1-\log DC1 \quad (23)$$

$$Adc2=\log(lical2/DC2)=\log lical2-\log DC2 \quad (24)$$

$$Adc3=\log(lical3/DC3)=\log lical3-\log DC3 \quad (25)$$

In a case where the apparatus has a circuit configuration which does not cause any change in the current flowing through the light-emitting elements (LEDs 20a, 20b, and 20c), the incident light intensities lical1, lical2, lical3 determined in step 1B are used in their unmodified forms.

However, in view of the fact that the living tissue involves an individual difference, a difference may arise between the electric currents Ccal1, Ccal2, Ccal3 flowing to the light-emitting elements when the incident light intensity measurement is performed through use of the phantom 30A (i.e., at the time of calibration), and electric currents Cmeas1, Cmeas2, Cmeas3 flowing to the light-emitting elements when the attenuation of the living body is measured (i.e., at the time of measurement). In a case where the apparatus has a circuit configuration for performing adjustment so as to achieve an optimum transmitted light intensity by changing the electric current of the light-emitting element, the incident light intensities liA1, liA2, liA3 employ values which have been corrected in accordance with the electric current values flowing through the light-emitting elements. Here, liA1, liA2 and liA3 are expressed by following Equations.

$$liA1=lcal1 \cdot Cmeas1/Ccal1 \quad (26)$$

$$liA2=lcal2 \cdot Cmeas2/Ccal2 \quad (27)$$

$$liA3=lcal3 \cdot Cmeas3/Ccal3 \quad (28)$$

Even in this step, computation of the DC attenuations Adc1, Adc2, Adc3 is performed per each wave of the pulsating transmitted light intensities lt1, lt2, lt3; that is, per each heartbeat.

In subsequent step 4B, the CPU 140 calculates a concentration of carboxyhemoglobin COHbdc through use of following Equation (29), which employs, as variables, Φ12 and Φ13 determined in step 2B and the DC attenuations Adc1, Adc2, Adc3 determined in step 3B.

$$COHbdc=a6 \cdot \Phi12+b6 \cdot \Phi13+c6+d6 \cdot Adc2/Adc1+ e6 \cdot Adc3/Adc1 \quad (29)$$

Coefficients a6, b6, c6, d6, and e6 of Equation (29) are values which have been determined beforehand by the method of least squares so as to minimize a difference between the carboxyhemoglobin concentration COHbdc determined by calculating a certain population (e.g., data pertaining to ten selected persons) through use of Equation (29) and the accurate concentration of carboxyhemoglobin COHbs measured through blood sampling.

Here, in order to exhibit the advantageous effect of the apparatus, the concentration of carboxyhemoglobin calculated through use of only the attenuation variation ratios Φ12 and Φ13 of the pulse wave is compared with the concentration of carboxyhemoglobin determined by blood sampling. Further, the concentration of carboxyhemoglobin calculated by the apparatus through use of Φ12, Φ13 and the DC attenuations Adc1, Adc2, Adc3 is compared with the concentration of hemoglobin determined by blood sampling.

When only the attenuation variation ratios Φ12, Φ13 are used, the concentration of carboxyhemoglobin is calculated by Equation (30).

$$COHbp=a7 \cdot \Phi12+b7 \cdot \Phi13+c7 \quad (30)$$

Figure 8A:
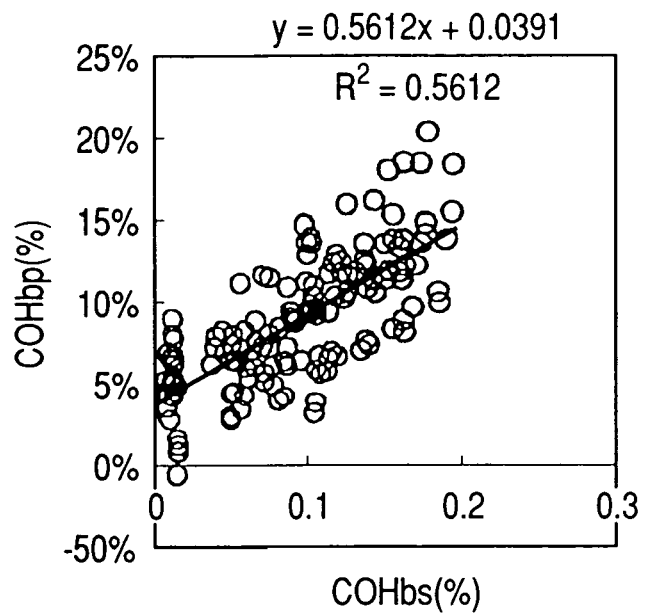
FIGS. 8A and 8B are views for explaining the advantageous effect obtained by the apparatus of the second embodiment.

Coefficients a7, b7, c7 employed in this case are also determined in advance on the basis of the data pertaining to the population in the same manner as that mentioned previously. FIG. 8A shows a correlation between the carboxyhemoglobin concentration COHbp calculated through use of Equation (30) and the carboxyhemoglobin concentration COHbs measured by blood sampling.

Figure 8B:
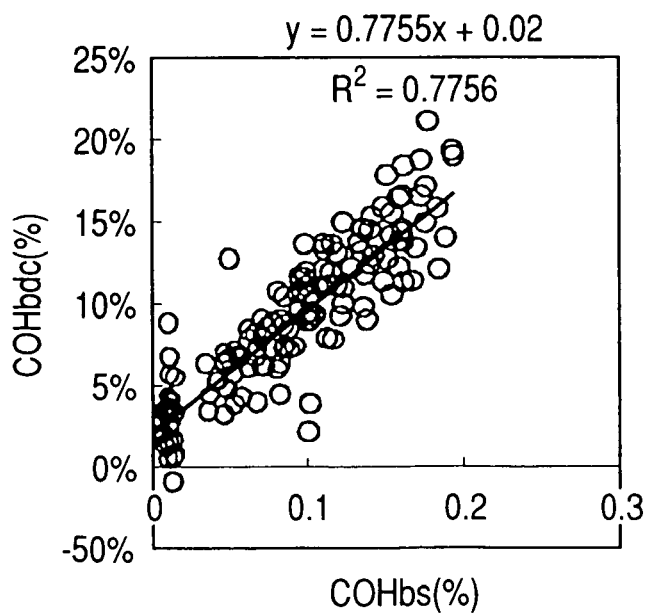

FIG. 8B shows a correlation between the carboxyhemoglobin concentration COHbc determined by the apparatus based on Equation (29) through use of the DC attenuations and the carboxyhemoglobin concentration COHbs measured by blood sampling.

As is evident from a comparison between the drawings, an improvement is achieved in a match between the carboxyhemoglobin concentration determined by the apparatus and that determined by blood sampling, by taking the DC attenuations into Equations.

The following equation may be employed in lieu of Equation (29).

$$COHbdc=a8 \cdot \Phi12+b8 \cdot \Phi13+c8+d8 \cdot Adc1+e8 \cdot Adc2+ f8 \cdot Adc3 \quad (31)$$

Coefficients a8, b8, c8, d8, e8, f8 of this equation have been determined beforehand in the same manner as mentioned previously.

A constant reverse correlation exists between the DC attenuations Adc1, Adc2, Adc3 and the DC transmitted light intensities DC1, DC2, DC3. Hence, there is yielded the same effect as that achieved by performing calculating operation through use of the DC transmitted light intensities in their unmodified forms without computation of the attenuations. In this case, the DC transmitted light intensity is proportional to the intensity of the light incident on the probe. Therefore, the incident light intensities must be corrected, while being normalized, by a specific current value flowing into the light-emitting elements (the LEDs 20a, 20b, and 20c). The corrected DC transmitted light intensities ltcomp1, ltcomp2, ltcom3 for the respective wavelengths are calculated by following Equations (32) to (34).

$$ltcomp1=DC1(lical1/lstd1)(Cmeas1/Ccal1) \quad (32)$$

$$ltcomp2=DC2(lical2/lstd2)(Cmeas2/Ccal2) \quad (33)$$

$$ltcomp3=DC3(lical3/lstd3)(Cmeas3/Ccal3) \quad (34)$$

Here, DC1, DC2, DC respectively denote measured DC transmitted light intensities; lical1, lical2, lical3 respectively denote incident light intensities calculated at the time of calibration; lstd1, lstd2, lstd3 respectively denote standard incident light intensities; Cmeas1, Cmeas2, Cmeas3 respectively denote current values flowing into light-emitting elements obtained when measurement is performed on a living body; and Ccal1, Ccal2, Ccal3 respectively denote current values flowing into the light-emitting elements obtained at the time of calibration of the incident light intensities.

Therefore, following Equations (35) and (36) may be employed in place of Equations (29) and (31).

$$COHbdc = a9 \cdot \Phi12 + b9 \cdot \Phi13 + c9 + d9 \cdot lt\text{comp}1/lt\text{comp}2 + e9 \cdot lt\text{com}1/lt\text{comp}3 \quad (35)$$

$$COHbdc = a10 \cdot \Phi12 + b10 \cdot \Phi13 + c10 + d10 \cdot lt\text{comp}1 + e10 \cdot lt\text{comp}2 + f10 \cdot lt\text{comp}3 \quad (36)$$

Here, coefficients a9 to e9 in Equation (35) and coefficients a10 to f10 in Equation (36) are determined in advance in the same manner as mentioned previously and through use of data pertaining to a population analogous to those mentioned previously.

Even in this step, computation of COHbdc is performed per each wave of the pulsating transmitted light intensities lt1, lt2, lt3; that is, per each heartbeat. The CPU 140 stores the thus-determined COHbdc into the memory 150 and displays the same on the display 160.

According to the apparatus of the embodiment, the concentration of carboxyhemoglobin is calculated through use of the DC attenuation or DC transmitted light intensity achieved at the first wavelength 940 nm at which light is absorbed by blood, the DC attenuation or DC transmitted light intensity achieved at the second wavelength 660 nm at which light is absorbed by blood, and the DC attenuation or DC transmitted light intensity achieved at the third wavelength 620 nm at which light is absorbed by blood. As a result, consideration has been given to the thickness of the entire blood layer located at an area to be measured, whereby the concentration of carboxyhemoglogin can be measured accurately.

A third embodiment of the invention will now be described. The third embodiment is directed to an apparatus for measuring a dye concentration. This apparatus employs light beams having three wavelengths as in the case of the second embodiment, the entire configuration of the apparatus is the same as shown in FIG. 6, and the repetitive explanations will be omitted.

Figure 9:
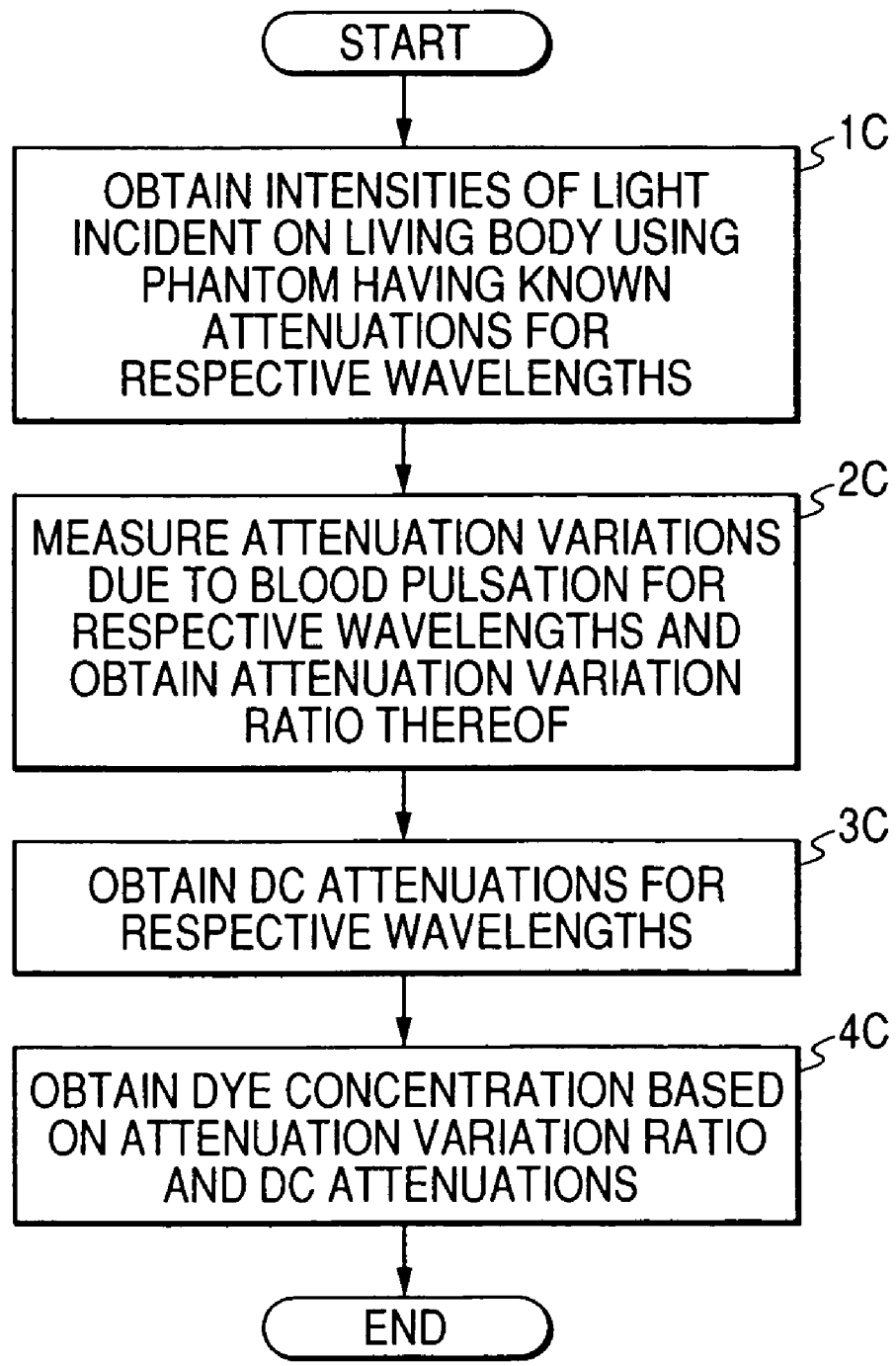
FIG. 9 is a flow chart for explaining a processing flow of an apparatus of the third embodiment.

However, as shown in FIG. 9, a program of processing to be performed by the CPU 140 differs from that described in the second embodiment. Moreover, the first wavelength assumes a value of 940 nm; the second wavelength assumes a value of 660 nm; and the third wavelength assumes a value of 805 nm. Operation of the apparatus will be described hereinbelow by reference to FIG. 9.

In step 1C, the intensity of the light incident on the living body 30 is measured. As in the case of step 1B to be performed by the apparatus of the second embodiment, the incident light intensities lical1, lical2, lical3 of the three light beams having different wavelengths are determined through use of the phantom 30A, and the thus-determined incident light intensities are stored in the memory 150.

In next step 2C, after having attached the probe to the living body 30, the operator infuses a dye into the blood of the living body 30. For instance, indocyanine green is used as a dye. A ratio between changes in the attenuations of the respective wavelengths is determined in the same manner as in step 2B of the second embodiment. Specifically, $\Phi12$ and $\Phi13$ are determined by Equations (21) and (22), and results of computation are stored in the memory 150.

In this step, computation of $\Phi12$, $\Phi13$ is performed per each wave of the pulsating transmitted light intensities lt1, lt2, lt3; that is, per each heartbeat.

In subsequent step 3C, the DC attenuations Adc1, Adc2, Adc3 of the respective wavelengths are determined. Here, the CPU 140 calculates the DC attenuations Adc1, Adc2 of the respective wavelengths by substituting, into following Equations (23) to (25) in the same manner as in the step 3B of the second embodiment.

When the apparatus has a circuit configuration which does not cause any change in the current flowing through the light-emitting elements (LEDs 20a, 20b, and 20c), the incident light intensities lical1, lical2, lical3 determined in step 1C are used as they are, as previously mentioned.

However, in view of the fact that the living tissue involves an individual difference, a difference may arise between the electric currents Ccal1, Ccal2, Ccal3 flowing to the light-emitting elements when the incident light intensity measurement is performed through use of the phantom 30A (i.e., at the time of calibration), and electric currents Cmeas1, Cmeas2, Cmeas3 flowing to the light-emitting elements when the attenuation of the living body is measured (i.e., at the time of measurement). In a case where the apparatus has a circuit configuration for performing adjustment so as to achieve an optimum transmitted light intensity by changing the electric current of the light-emitting element, the incident light intensities liA1, liA2, liA3 employ values which have been corrected in accordance with the electric current values flowing through the light-emitting elements. Here, liA1, liA2 and liA3 are expressed by Equations (26) through (28).

Even in this step, computation of the DC attenuations Adc1, Adc2, Adc3 is performed per each wave of the pulsating transmitted light intensities lt1, lt2, lt3; that is, per each heartbeat.

In subsequent step 4C, the CPU 140 calculates the concentration of a dye Cddc through use of following Equation (37), which employs, as variables, $\Phi12$ and $\Phi13$ determined in step 2C and the DC attenuations Adc1, Adc2, Adc3 determined in step 3C.

$$Cddc = a11 \cdot \Phi12 + b11 \cdot \Phi13 + c11 + d11 \cdot Adc2/Adc1 + e11 \cdot Adc3/Adc1 \quad (37)$$

Coefficients a11 to e11 of Equation (37) are values which have been determined beforehand by the method of least squares so as to minimize a difference between the concentration of a dye Cddc determined by calculating a certain population (e.g., data pertaining to ten selected persons) through use of Equation (37) and the accurate concentration of a dye Cds measured through blood sampling.

Here, in order to exhibit the advantageous effect of the present apparatus, the concentration of dye calculated through use of only the attenuation variation ratios $\Phi12$, $\Phi13$ of the pulse wave and the concentration of dye calculated through use of the attenuation variation ratios $\Phi12$, $\Phi13$ and the DC attenuations Adc1, Adc2, Adc3 of the present apparatus are compared with the concentration of dye determined by blood sampling.

When only the attenuation variation ratios $\Phi12$, $\Phi13$ are used, the concentration of a dye is calculated by Equation (38).

$$Cdp = a12 \cdot \Phi12 + b12 \cdot \Phi13 + c12 \quad (38)$$

Figure 10A:
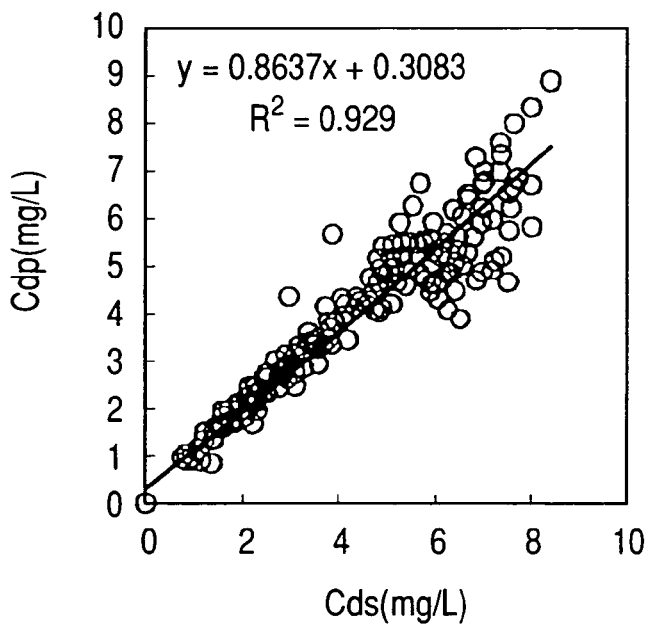
FIGS. 10A and 10B are views for explaining the advantageous effect obtained by the apparatus of the third embodiment.
Figure 10B:
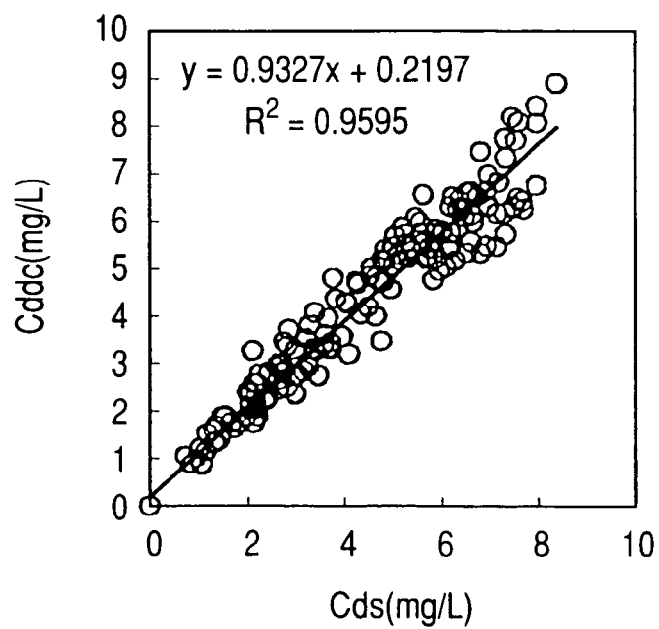

Coefficients a12, b12, c12 employed in this case are also determined in advance on the basis of the data pertaining to the population in the same manner as that mentioned previously. FIG. 10A shows a correlation between the dye concentration Cdp calculated through use of Equation (38) and the dye concentration Cds measured by blood sampling. FIG. 10B shows a correlation between the dye concentration Cddc determined by the apparatus through Equation (37) and the dye concentration Cds measured by blood sampling.

As is evident from a comparison between the drawings, improvement is achieved in a match between the dye concentration determined by the apparatus and that determined by blood sampling, by taking the DC attenuations into Equations.

Moreover, following Equation (39) may be employed in lieu of Equation (37).

$$Cddc = a13\cdot\Phi12 + b13\cdot\Phi13 + c13 + d13\cdot Adc1 + e13\cdot Adc2 + f13\cdot Adc3 \quad (39)$$

Coefficients a13 to f13 of this equation have been determined beforehand in the same manner as mentioned previously.

A constant reverse correlation exists between the DC attenuations Adc1, Adc2, Adc3 and the DC transmitted light intensities DC1, DC2, DC3. Hence, there is yielded the same effect as that achieved by performing calculating operation through use of the DC transmitted light intensities in their unmodified forms without computation of the attenuations. In this case, the DC transmitted light intensity is proportional to the intensity of the light incident on the probe. Therefore, the incident light intensities must be corrected, while being normalized, by a specific current value flowing into the light-emitting elements (the LEDs $20a$, $20b$, and $20c$). The corrected DC transmitted light intensities Itcomp for the respective wavelengths are calculated by following Equations (40) through (42).

$$It\text{comp}1 = DC1(lical1/lstd1)(Cmeas1/Ccal1) \quad (40)$$

$$It\text{comp}2 = DC2(lical2/lstd2)(Cmeas2/Ccal2) \quad (41)$$

$$It\text{comp}3 = DC3(lical3/lstd3)(Cmeas3/Ccal3) \quad (42)$$

Here, DC1, DC2, DC respectively denote measured DC transmitted light intensities; lical1, lical2, lical3 respectively denote incident light intensities calculated at the time of calibration; lstd1, lstd2, lstd3 respectively denote standard incident light intensities; Cmeas1, Cmeas2, Cmeas3 respectively denote current values flowing into light-emitting elements obtained when measurement is performed on a living body; and Ccal1, Ccal2, Ccal3 respectively denote current values flowing into the light-emitting elements obtained at the time of calibration of the incident light intensities.

Therefore, following Equations (43) and (44) may be employed in place of Equations (37) and (39).

$$Cddc = a14\cdot\Phi12 + b14\cdot\Phi13 + c14 + d14\cdot It\text{comp}1/It\text{comp}2 + e14\cdot It\text{com}1/It\text{comp}3 \quad (43)$$

$$Cddc = a15\cdot\Phi12 + b15\cdot\Phi13 + c15 + d15\cdot It\text{comp}1 + e15\cdot It\text{comp}2 + f15\cdot It\text{comp}3 \quad (44)$$

Here, coefficients a14 to e14 in Equation (43) and coefficients a15 to f15 in Equation (44) are determined in advance in the same manner as mentioned previously and through use of data pertaining to a population analogous to those mentioned previously.

Even in this step, computation of Cddc is performed per each wave of the pulsating transmitted light intensities lt1, lt2, lt3; that is, per each heartbeat. The CPU 140 stores the thus-determined Cddc into the memory 150 and displays the same on the display 160.

According to the apparatus of the embodiment, the concentration of a dye is calculated through use of the DC attenuation or DC transmitted light intensity achieved at the first wavelength 940 nm at which light is absorbed by blood, the DC attenuation or DC transmitted light intensity achieved at the second wavelength 805 nm at which light is absorbed by blood, and the DC attenuation or DC transmitted light intensity achieved at the third wavelength 660 nm at which light is absorbed by blood. As a result, consideration has been given to the thickness of the entire blood layer located at an area to be measured, whereby the concentration of dye can be measured accurately.

The above descriptions have described the cases where the intensity of the light irradiated onto the living body is changed by controlling the electric current values flowing through the light-emitting elements. However, the incident light intensities and the DC transmitted light intensities, which are to be measured, may be corrected in accordance with the value of a voltage by controlling the voltage applied to the light-emitting elements to thereby change the intensity of light beams of the light-emitting elements.

What is claimed is:

1. An apparatus for measuring a concentration of a light-absorbing substance in blood, comprising:
    a light emitter, adapted to irradiate a living tissue with (n) light beams, at least one of the light beams having a wavelength which is absorbed by the blood;
    a first instrument, which measures (n) first intensities of the light beams, which are to be incident on the living tissue;
    a second instrument, which measures (n) second intensities of the light beams, which are transmitted through the living tissue;
    a first calculator, which calculates at least one but at most (n−1) attenuation variation ratio, which is a ratio of attenuation variations of the respective light beams due to variation of a volume of the blood caused by pulsation, based on the second intensities of the light beams with reference to DC light levels thereof; and
    a second calculator, which calculates, at least one but at most, (n) DC components of attenuations of the light beams, based on the first intensities and the second intensities, and obtains the concentration based on the DC components and the attenuation variation ratio.

2. The apparatus as set forth in claim 1, wherein:
    the light emitter comprises light emitting elements, and a controller which controls a current value or a voltage value supplied to the light emitting elements; and
    the second calculator corrects the first intensities in accordance with the current value or the voltage value.

3. The apparatus as set forth in claim 1, wherein:
    the second instrument measures third intensities of the light beams which are transmitted through a phantom placed between the light emitter and the second instrument; and
    the first instrument obtains the first intensities based on the third intensities.

4. The apparatus as set forth in claim 3, wherein:
    the first instrument comprises a sensor which senses whether the phantom is placed between the light emitter and the second instrument; and
    the first instrument begins calculation to obtain the first intensities when the sensor senses that the phantom is placed between the light emitter and the second instrument.

5. The apparatus as set forth in claim 1, wherein the light beams include a light beam having a wavelength which is absorbed by a living tissue other than the blood.

6. An apparatus for measuring a concentration of a light-absorbing substance in blood, comprising:

a light emitter, adapted to irradiate a living tissue with (n) light beams, at least one of the light beams having a wavelength which is absorbed by the blood;

a first instrument, which measures (n) first intensities of the light beams, which are to be incident on the living tissue;

a second instrument, which measures (n) second intensities of the light beams, which are transmitted through the living tissue;

a first calculator, which calculates at least one but at most (n−1) attenuation variation ratio, which is a ratio of attenuation variations of the respective light beams due to variation of a volume of the blood caused by pulsation, based on the second intensities of the light beams with reference to DC light levels thereof; and a second calculator, which calculates, at least one but at most, (n) third intensities of the light beams, based on the first intensities which are obtained when the apparatus is subjected to calibration, DC components of the second intensities and current values supplied to the light emitter to emit the light beams, and obtains the concentration based on the third intensities and the attenuation variation ratio.

7. The apparatus as set forth in claim 6, wherein the light beams include a light beam having a wavelength which is absorbed by a living tissue other than the blood.

* * * * *